Figure 3:
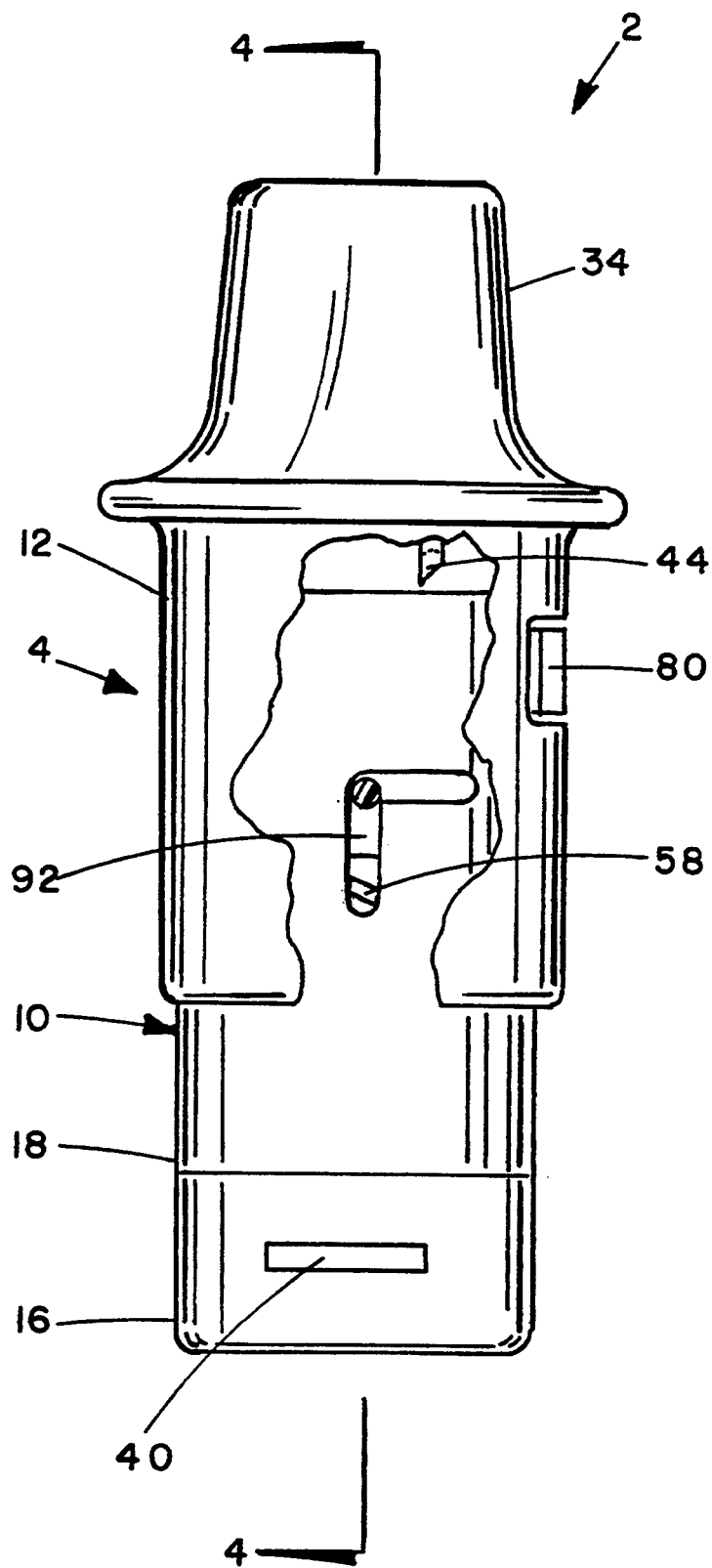
Figure 4:
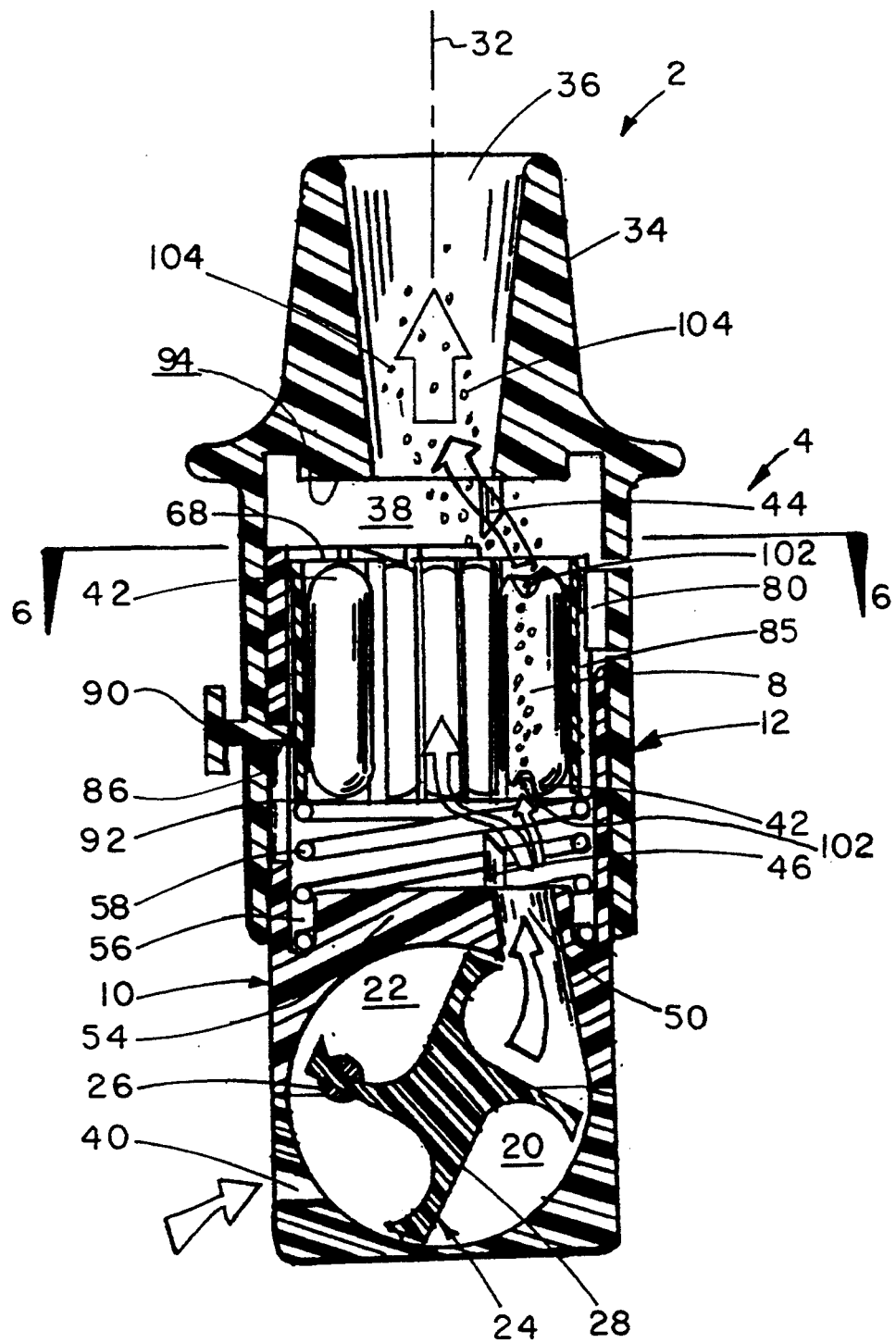

United States Patent [19]

Haber et al.

[11] Patent Number: 5,372,128
[45] Date of Patent: Dec. 13, 1994

[54] FLUIDIZING POWDER INHALER

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 47,123

[22] Filed: Apr. 14, 1993

[51] Int. Cl.$^5$ .......................................... A61M 15/00
[52] U.S. Cl. ........................ 128/203.21; 128/203.15
[58] Field of Search ............... 128/203.15, 203.21, 128/200.24, 203.12, 203.23; 604/58

[56]  References Cited

U.S. PATENT DOCUMENTS

| | | | |
|---|---|---|---|
| 16,066 | 11/1856 | Murphy | 128/203.15 |
| 3,518,992 | 9/1970 | Altounyan et al. | 128/203.21 |
| 3,669,113 | 6/1972 | Altounyan | 128/203.15 |
| 3,837,341 | 9/1974 | Bell | 128/203.15 |
| 3,858,583 | 1/1975 | Hallworth et al. | 128/203.15 |
| 3,870,046 | 3/1975 | Elliott | 128/203.15 |
| 3,888,253 | 6/1975 | Watt | 128/203.15 |
| 3,948,264 | 4/1976 | Wilke | 128/203.15 |
| 4,116,195 | 9/1978 | James | 604/244 |
| 4,117,844 | 10/1978 | James | 128/203.15 |
| 4,338,931 | 7/1982 | Cavazza | 128/203.15 |
| 4,446,862 | 5/1984 | Baum | 128/203.15 |
| 4,627,432 | 12/1986 | Newell | 128/203.15 |
| 4,811,731 | 3/1989 | Newell et al. | 128/203.15 |
| 4,860,740 | 8/1989 | Kirk | 128/203.15 |
| 4,884,565 | 12/1989 | Cocozza | 128/203.21 |
| 5,035,237 | 7/1991 | Newell et al. | 128/203.15 |
| 5,048,514 | 9/1991 | Ramella | 128/203.21 |
| 5,207,217 | 4/1993 | Cocozza et al. | 128/203.21 |

FOREIGN PATENT DOCUMENTS

| | | | |
|---|---|---|---|
| 1268051 | 3/1972 | United Kingdom | 128/203.15 |
| 2061735 | 5/1981 | United Kingdom | 128/203.15 |

OTHER PUBLICATIONS

Spinhaler ® Turbo-Inhaler instruction leaflet, Fisons Corporati.

*Primary Examiner*—Edgar S. Burr
*Assistant Examiner*—Eric P. Raciti
*Attorney, Agent, or Firm*—Townsend & Townsend Khourie & Crew

[57] ABSTRACT

An inhaler (2) is used with dry pharmaceutical-containing capsules (8) carried by a cassette (6) within the body of the inhaler. The inhaler defines an air path from an air inlet (40) to an air/pharmaceutical outlet (36). The air path passes a dispensing position (48) at which capsules are positioned successively. To dispense the pharmaceutical both ends of an elongated capsule are pierced with spikes (44, 46). The patient then places in his or her mouth over the outlet, inhales and draws air through the inlet, axially through and along the breached capsule at the dispensing position and pulls a mixture of air and powdered pharmaceutical through the outlet and into the lungs. To aid entrainment of the dry pharmaceutical (104) into the air stream, a vibration mechanism, such as an imbalanced rotor (24) adjacent the air inlet which rotates and vibrates due to the passing air, is used.

16 Claims, 5 Drawing Sheets

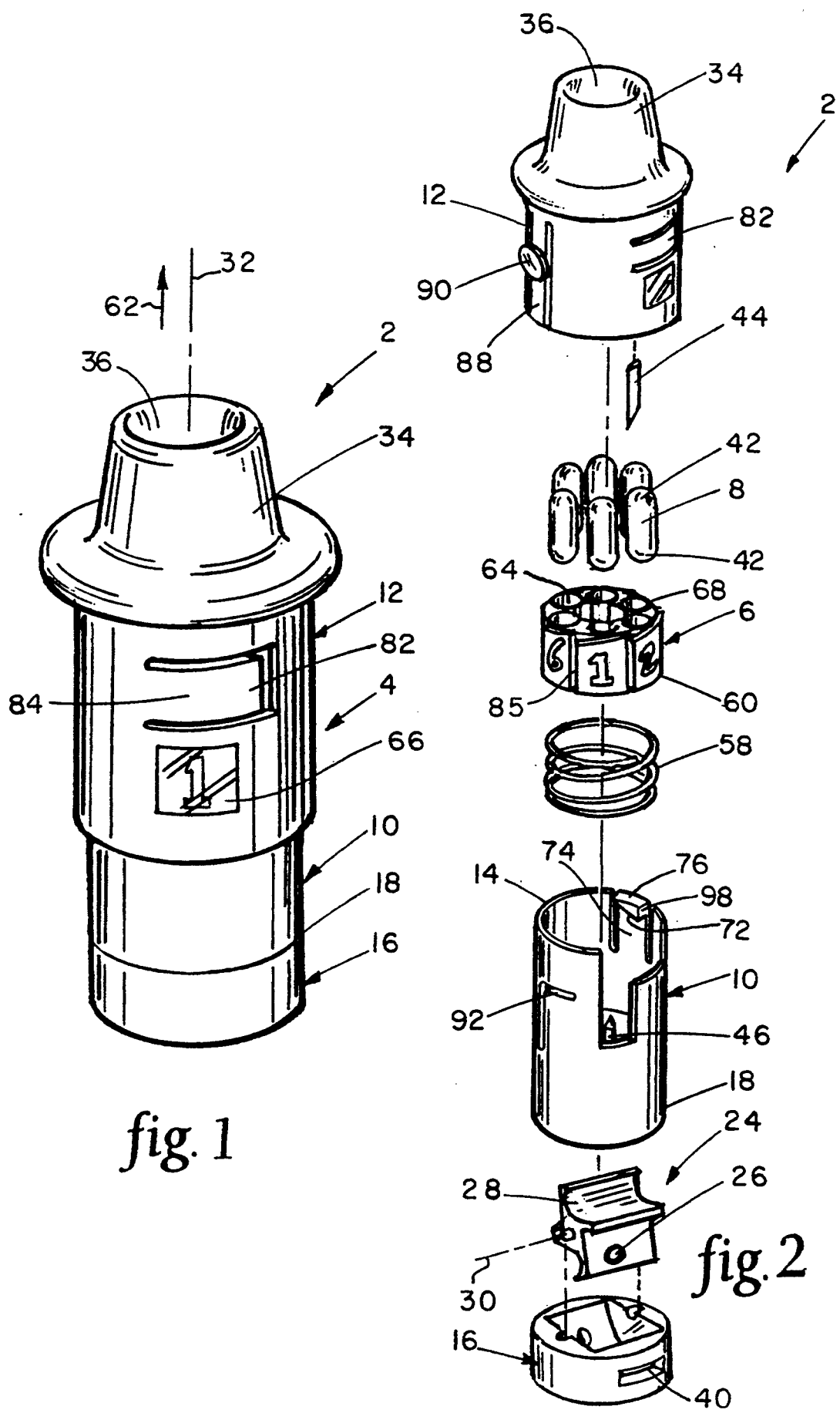

FLUIDIZING POWDER INHALER

CROSS-REFERENCE TO RELATED APPLICATIONS

This is related to U.S. patent application No. 07/747,375 now U.S. Pat. No. 5,287,850 for TIMING AND VELOCITY CONTROLLED POWDERED PHARMACEUTICAL INHALER, the disclosure of which is incorporated by reference.

BACKGROUND OF THE INVENTION

Some pharmaceuticals are best delivered in powdered form directly into the lungs of a patient. Conventional inhalers often use a measured dose of a powdered pharmaceutical from a capsule for delivery of the pharmaceutical to the patient. Access to the powdered pharmaceutical is often by piercing the sides of the capsules. Also, the two halves of the capsules can be separated to permit access to the powdered pharmaceutical.

SUMMARY OF THE INVENTION

The present invention is directed to an inhaler which is simple in construction, can accommodate cassettes holding multiple capsules and is very effective at delivery of the powdered pharmaceutical from the capsules.

The inhaler is used with pharmaceutical-containing capsules carried within a cassette within the body of the inhaler. The inhaler has an air inlet and an air/pharmaceutical outlet. An inhaler defines an air path from the inlet to the outlet. The air path passes a dispensing position at which capsules are positioned successively. To dispense the pharmaceutical, both ends of the elongated capsules are first breached, typically by piercing with spikes. The patient then places in his or her mouth over the outlet, inhales and draws air through the inlet, past the breached cassette at the dispensing position and pulls a mixture of air and powdered pharmaceutical through the outlet and into the lungs. The air path at the dispensing position is parallel to the capsules so that the air flows axially along and through the breached capsule. To aid movement of the pharmaceutical from the breached capsule into the air stream passing axially along the breached capsule, a vibration mechanism is supplied. In the preferred embodiment an imbalanced rotor adjacent the air inlet rotates due to the air moving along the air path and vibrates due to the imbalance of the rotor.

One of the primary advantages of the invention is that the pharmaceutical containing capsules can be housed within cassettes which hold multiple capsules. The inhaler can be designed so that when each of the capsules in the cassette has been used, the cassette can be easily removed and replaced with a new capsule-containing cassette. Another advantage results from the use of the out-of-balance rotor to induce lateral vibrations of the capsules for maximizing the effectiveness of vibration fluidization of the powdered pharmaceutical particles. The rotor is preferably positioned adjacent the air inlet, that is upstream of the capsules, so that the rotor is not contaminated with moisture or pharmaceutical particles.

Accordingly, the invention is directed to two main aspects. The first aspect is the breaching of the ends of the capsule and the positioning of the capsule parallel to the air path to provide efficient pharmaceutical particle aspiration at lower air stream velocities. The second aspect pertains to the use of an off-balance rotor to provide vibration, in particular lateral vibration, to the breached cartridge for efficient fluidization of the powdered pharmaceutical particles.

Other features and advantages of the invention will appear from the following description in which the preferred embodiment has been set forth in detail in conjunction with the accompanying drawings.

BRIEF DESCRIPTION OF THE DRAWINGS

FIG. 1 is an isometric view of an inhaler made according to the invention;

FIG. 2 is an exploded isometric view of the inhaler of FIG. 1;

FIG. 3 is an enlarged side view of the inhaler of FIG. 2 with a portion of the outlet case broken away to show the L-shaped track in the rotor case and the cassette holding arm;

FIG. 4 is a cross-sectional view of the inhaler of FIG. 3 illustrating the rotor in cross section and the spikes prior to piercing the ends of a capsule prior to an inhalation sequence;

FIG. 5 is top plan view of the capsule holding cassette of FIG. 1;

FIG. 5A is a side elevational view of the cassette of FIG. 5 illustrating the ramped surfaces, alignment grooves and dose numbers;

FIG. 6 is a cross-sectional view taken along line 6—6 of FIG. 4; and FIG. 7 is top plan view of the rotor case showing the relationship of a spike and the rotor chamber outlet.

DESCRIPTION OF THE PREFERRED EMBODIMENT

An overview of a powdered pharmaceutical inhaler 2 and its use will first be given followed by a more detailed discussion. Inhaler 2 includes a body 4 housing a cassette 6 which holds six powdered pharmaceutical-containing capsules 8. Body 4 includes a rotor case 10 and an outlet case 12 slidably mounted over the proximal end 14 of case 10. A rotor base 16 is secured to the distal end 18 of rotor case 10, such as with an adhesive. As shown in FIGS. 1 and 4, rotor base 16 and distal end 18 of rotor case 10 define semi-cylindrical regions 20, 22. An out-of-balance rotor 24 is freely rotatably mounted within regions 20, 22. Rotor 24 has an eccentrically positioned weight 26 mounted on one of its blades 28 so that rotation of rotor 24 causes inhaler 2 to vibrate. The radial or transverse positioning of the axis of rotation 30 of rotor 24 relative to the central axis 32 of inhaler 2 causes the vibrations created by out-of-balance rotor 24 to shake or vibrate inhaler 2 laterally relative to central axis 32. The significance of this will be discussed below.

Just prior to use, a capsule 8 is first breached at its distal ends 42 by spikes 44, 46 and is moved to a pharmaceutical dispensing position 48, shown in FIG. 4. To draw air through inhaler 2, the user initially covers inlet 40 with a finger. The user then places his or her mouth over mouthpiece 34 of outlet case 12 which defines an air/pharmaceutical outlet 36 therein. Inhaling on mouthpiece 34 and then uncovering inlet 40 causes air to be suddenly pulled into the interior 38 of inhaler 2 through an air inlet 40, through regions 20, 22, causing rotor 24 to spin and thus vibrate inhaler 2, through a rotor chamber outlet 50, past cassette 6 and the breached capsule 8 at dispensing position 48, out through outlet 36 and into the mouth and lungs of the patient. Air passes both axially through the breached capsule 8 and axially through the hollow center 52 of cassette 6. The initial covering of inlet 40 causes an initial rush of air through inhaler 2 for more effective operation.

Figure 7:
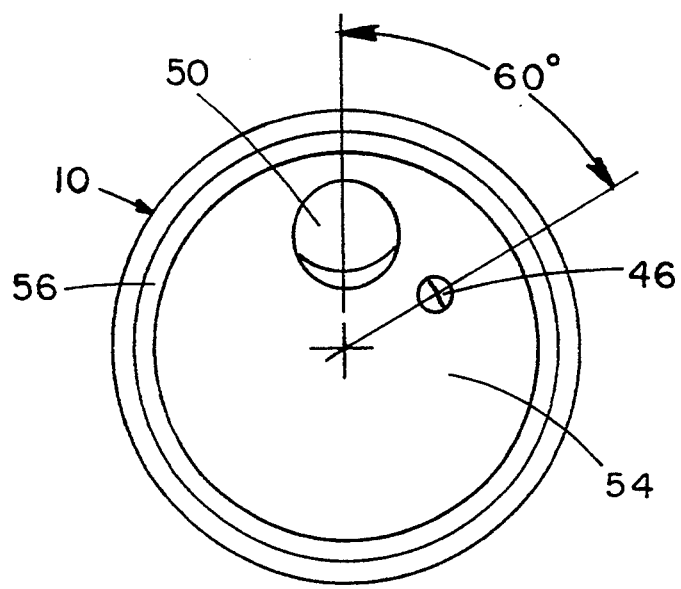

Inhaler 2 will now be described in somewhat more detail. Rotor case 10 includes a central barrier or bulkhead 54 having rotor chamber outlet 50 formed therein. Spike 46 is positioned near but about 60° offset from outlet 50 as shown in FIG. 7. A cirumferential groove 56 is formed in bulkhead 54 and is used to house one end of a compression spring 58. The other end of spring 58 presses against the distal end 60 of cassette 6 thus biasing cassette 6 in a proximal direction 62.

Figure 5:
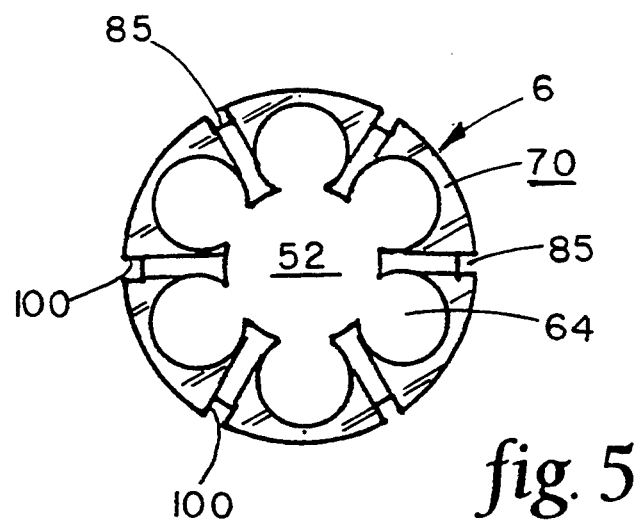
Figure 5A:
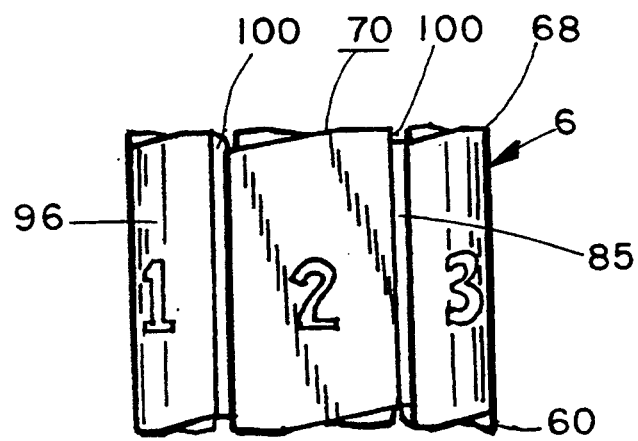

Cassette 6 has a series of six C-shaped openings 64, see FIG. 5, sized to accept capsules 8. With capsules 8 mounted in openings 64, cassette 6 still defines an axial bore through center 52 of cassette 6. The proximal end 68 of cassette 6 has six ramped surfaces 70 adjacent the six C-shaped openings 64. Cassette 6 has numerals 1–6 which are visible through a window 66 in outer case and through an L-shaped cut-out 78 formed in rotor case 10. Surfaces 70 are engaged by tapered surface 72 formed at the end of a resilient finger 74 at proximal end 14 of rotor case 10. Finger 74 and tapered surface 72 act as a cassette advance pawl 76 as discussed below.

Rotor case 10 has a relatively wide L-shaped cut-out 78 shown in FIG. 2. Cut-out 78 is aligned with an anti-reverse ratchet tooth 80 extending inwardly and formed at the free end 82 of a circumferentially extending spring finger 84. Spring finger 84 is formed as an integral part of outlet case 12 and is positioned so that ratchet finger 80 engages axially extending external grooves 85 formed in cassette 6. This engagement prevents cassette 6 from rotating with rotor case 10 when rotor case 10 is rotated relative to outlet case 12 in a counterclockwise direction when viewing inhaler 2 from rotor base 16, that is in proximal direction 62.

Outlet case 12 also includes an inwardly extending guide pin 86 at one end of an axially extending spring finger 88 formed as an integral part of outlet case 12. A knob 90 is also formed at the end of spring finger 88 but on the outside of outlet case 12. Knob 90 allows the user to pull guide pin 86 from within an L-shaped slot 92 formed in rotor case 10. Doing so permits the user to separate outlet case 12 from rotor case 10, such as when replacing cassette 6. The engagement of guide pin in slot 92 limits the relative movement of rotor case 10 and outlet case 12 to about 60° in a rotary direction and about 0.45 cm in an axial direction. Enlarged cut-out 78 is likewise sized to accommodate ratchet tooth 80 during similar relative movement of rotor case 10 and outlet case 12.

Assuming inhaler 2 has a full cassette 6 of capsules 8, preparatory to use the user presses mouthpiece 34 towards rotor base 16. Doing so initially causes outlet case 12 to slide over rotor case 10 with pin 86 moving along the axial portion of slot 92 and ratchet finger 80 moving along the axial portion of cut-out 78. As this movement continues, spike 44 breaches one of the ends 42 of the capsule 8 aligned with spikes 44, 46. Spikes 44, 46 are shaped so they cleanly pierce ends 42 of capsules 8 rather than sliding off and deforming the ends. Once an abutment surface 94 of outlet case 12 contacts proximal end 68 of cassette 6, continued movement of mouthpiece 34 towards rotor base 16 forces cassette 6 against spring 58 causing spike 46 to pierce or breach the other end 42 of capsule 8. At the end of the stroke, which is limited by guide pin 86 within the axial portion of slot 92, the user releases cases 10, 12 and then pulls the cases apart back to the starting position with guide pin 86 at the proximal end of slot 92.

Viewing inhaler 2 from rotor base 16, that is looking in proximal direction 62, the user rotates rotor case 10 counter-clockwise relative to outlet case 12 until an audible click is heard. This movement causes cassette 6 to rotate 60° within rotor case 10 so that the newly breached capsule 8 becomes misaligned with spike 46, remains aligned with spike 44 and becomes aligned with rotor chamber outlet 50. This driving motion is created by the engagement of ratchet finger 80 with one of the six grooves 85. The clicking sound is created by pawl 76 riding up and over one of the ramped surfaces 70. This movement of pawl 76 is permitted because cassette 6 can move axially against spring 58 thus compressing spring 58 as pawl 76 moves from one stable position adjacent one groove 85 to another stable position adjacent the next groove 85.

Rotor case 10 is then turned clockwise 60° relative to outlet case 12. During this movement, ratchet finger 80 at the end of spring finger 88 slides over the outer surface 96 of cassette 6 going from engagement of one groove 85 to the adjacent groove 85 since the cassette is prevented from rotary movement relative to rotor case 10 during this activity by the engagement of an abutment surface 98 of pawl 76 with an abutment surface 100 formed at each of the proximal ends of grooves 85. The completion of this movement is signified by another click as ratchet finger 80 snaps back into the adjacent groove 85. At this point spikes 44, 46 are once again aligned over the next capsule 8 while the previously breached capsule is positioned over rotor chamber outlet 50.

Most of the parts of pharmaceutical inhaler 2 are made of a suitable plastic, such as polycarbonate. Weight 26, spikes 44, 46 and spring 58 are preferably stainless steel. Other suitable materials can also be used.

Figure 6:
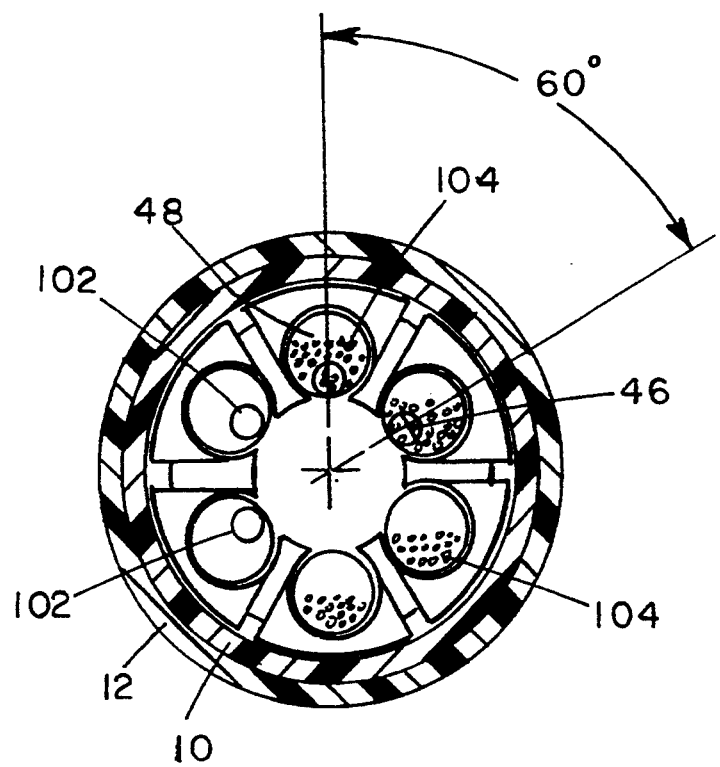

To use, the user first places his or her finger over air inlet slot 40 and positions inhaler 2 so that window 66 is facing up. This orients the pierced or breached capsule 8, which is aligned directly beneath window 66, at an uppermost position when the inhaler is held generally horizontally. As shown in FIG. 6, the opening 102 formed in ends 42 of capsule 8 are at a radially inward position so that gravity causes the powdered pharmaceutical 104 to become aligned with openings 102 when in this position. The user then places his or her mouth over mouthpiece 34 and inhales creating a partial vacuum within interior 38 of inhaler 2. The user then uncovers inlet 40 while continuing to inhale thus drawing air through air inlet 40, past rotor 24, through outlet 50, through the breached capsule 8 and axial bore 52 of cassette 6 to entrain powdered pharmaceutical 104 from the breached capsule 8. The mixture of air and powdered pharmaceutical then passes through air/pharmaceutical outlet 36 and into the lungs of the user. The air passing through regions 20, 22 causes rotor 24 to spin thus vibrating inhaler 2 due to the presence of weight 26. This vibration helps to fluidize and entrain the particles of dry pharmaceutical 104 within the breached capsule for enhanced aspiration into the lungs of the user.

Modification and variation can be made to the disclosed embodiment without departing from the subject of the invention as defined in the following claims. For example, outlet case 12 is shown to be an integral unit with mouthpiece 34. However, for ease of manufacture, these two pieces could be separately made and secured to one another during assembly. While it is preferred that the entire cassette 6 of capsules 8 be removed and replaced, first by pulling on knob 90 and separating outlet case 12 from rotor case 10 and then biasing pawl 76 outwardly to release the cassette, individual capsules 8 could be removed and replaced from the same or a different cassette 6. While a cassette 6 is shown with six capsules 8, a greater or lesser number of capsules could be used as well. Other structures for axially breaching capsules 8, preferably just prior to use, could be used as well. For example, cassette 6 could be made so that the distal ends 42 of capsules 8 extend past the ends 60, 68 of cassette 6 so that the act of rotating or indexing the cassette would cause the distal ends 42 of cassette 6 to be breached. If the breaching of capsules 8 creates bits and pieces of the capsule, appropriate filters can be used to ensure that the pieces of the capsules are not inhaled by the user.

What is claimed is:

1. An inhaler, for use with powdered pharmaceutical-containing capsules, the capsules each being elongated and having ends and a length therebetween, comprising:
   a body having an air inlet, an air/pharmaceutical outlet, a dispensing position and a hollow interior;
   means for directing air along an air path from the air inlet, past the dispensing position and through the air/pharmaceutical outlet;
   a capsule-holding cassette rotatably housed within the body, the cassette configured to carry a plurality of the capsules to a breaching position and to the dispensing position with the capsule lengths oriented generally coaxial with a portion of the air path at the dispensing position;
   means for breaching the ends of a capsule locatable at the breaching position; and
   means for incrementally rotating the cassette so to position successive capsules at the dispensing position, said capsules remaining within said cassette at the dispensing position;
   whereby movement of air along the air path from the air inlet, past and through the capsule with breached ends entrains the powdered pharmaceutical in the air and causes a combination of air and powdered pharmaceutical to pass through the air/pharmaceutical outlet.

2. The inhaler of claim 1 wherein the dispensing and breaching positions are different positions.

3. The inhaler of claim 1 wherein the cassette has a central through-bore.

4. An inhaler, for use with powdered pharmaceutical-containing capsules, the capsules each being elongated and having ends and a length therebetween, comprising:
   a body having an air inlet, an air/pharmaceutical outlet, a dispensing position and a hollow interior;
   means for directing air along an air path from the air inlet, past the dispensing position and through the air/pharmaceutical outlet;
   a capsule-holding cassette rotatably housed within the body, the cassette configured to carry a plurality of the capsules to a breaching position and to the dispensing position with the capsule lengths oriented generally coaxial with a portion of the air path at the dispensing position;
   the body including a first case rotatably mounted to a second case, the first case housing the cassette and having the air inlet and the second case having the air/pharmaceutical outlet;
   means for breaching the ends of a capsule locatable at a breaching position; and
   means for incrementally rotating the cassette so to position successive capsules at the dispensing position;
   whereby movement of air along the air path from the air inlet, past and through the capsule with breached ends entrains the powdered pharmaceutical in the air and causes a combination of air and powdered pharmaceutical to pass through the air/pharmaceutical outlet.

5. The inhaler of claim 4 wherein the incrementally rotating means incudes means for permitting the cassette to rotate within the first case only in a first rotary direction.

6. The inhaler of claim 5 further comprising means for limiting relative rotary motion between the first and second cases.

7. The inhaler of claim 4 wherein the breaching means includes first and second spikes adapted to pierce the ends of the capsule at the breaching position.

8. The inhaler of claim 7 further comprising means permitting the first and second cases to move axially relative to one another so to permit said spikes to pierce the ends of the capsule at the breaching position.

9. The inhaler of claim 1 wherein the breaching means includes first and second axially movable spikes adapted to pierce the ends of the capsule at the breaching position.

10. The inhaler of claim 1 further comprising means for vibrating the breached capsule while the air moves past and through the breached capsule.

11. The inhaler of claim 10 wherein the vibrating means includes an out-of-balance rotor positioned along the air path.

12. The inhaler of claim 11 wherein the rotor is positioned between the air inlet and the dispensing position.

13. An inhaler, for use with powdered pharmaceutical-containing capsules, comprising:
   a body having an air inlet, an air/pharmaceutical outlet, a dispensing position and a hollow interior;
   means for directing air along an air path from the air inlet, past the dispensing position and through the air/pharmaceutical outlet;
   a capsule-holding cassette rotatably housed within the body, the cassette configured to carry a plurality of the capsules to a breaching position and to the dispensing position;
   means for opening a capsule locatable at the breaching position;
   means for incrementally rotating the cassette so to position successive capsules at the dispensing position, said capsules remaining within said cassette at the dispensing position; and
   means for vibrating the opened capsule while the air moves past the breached capsule, the vibrating means including an out-of-balance rotor positioned along the air path;
   whereby movement of air along the air path from the air inlet, past the opened capsule entrains the powdered pharmaceutical in the air and causes a combination of air and powdered pharmaceutical to pass through the air/pharmaceutical outlet.

14. The inhaler of claim 13 wherein the rotor is positioned between the air inlet and the dispensing position.

15. An inhaler, for use with powdered pharmaceutical-containing capsules, the capsules each being elongated and having ends and a length therebetween, comprising:
- a body having an air inlet, an air/pharmaceutical outlet, a dispensing position and a hollow interior;
- means for directing air along an air path from the air inlet, past the dispensing position and through the air/pharmaceutical outlet;
- a capsule-holding cassette rotatably housed within the body, the cassette configured to carry a plurality of the capsules to a breaching position and to the dispensing position with the capsule lengths oriented generally coaxial with a portion of the air path at the dispensing position;
- means for piercing the ends of a capsule, locatable at the breaching position, using spikes;
- means for incrementally rotating the cassette so to position successive capsules at the dispensing position, said capsules remaining within said cassette at the dispensing position; and
- means for vibrating the pierced capsule while the air moves past and through the pierced capsule;
- whereby movement of air along the air path from the air inlet, past and through the capsule with breached ends entrains the powdered pharmaceutical in the air and causes a combination of air and powdered pharmaceutical to pass through the air/pharmaceutical outlet.

16. The inhaler of claim 15 wherein the vibrating means including an out-of-balance rotor positioned along the air path.

* * * * *